United States Patent
Jung et al.

(10) Patent No.: US 8,999,129 B2
(45) Date of Patent: Apr. 7, 2015

(54) LIQUID AND GEL ELECTRODES FOR TRANSVERSE FREE FLOW ELECTROPHORESIS

(75) Inventors: Byoungsok Jung, San Jose, CA (US); Klint A. Rose, Alviso, CA (US); Maxim Shusteff, Oakland, CA (US); Alexandre Persat, Palo Alto, CA (US); Juan Santiago, Stanford, CA (US)

(73) Assignees: Lawrence Livermore National Security, LLC, Livermore, CA (US); The Board of Trustees of the Leland Stanford Junior University, Palo Alto, CA (US)

( * ) Notice: Subject to any disclaimer, the term of this patent is extended or adjusted under 35 U.S.C. 154(b) by 349 days.

(21) Appl. No.: 13/413,161

(22) Filed: Mar. 6, 2012

(65) Prior Publication Data

US 2012/0228141 A1 Sep. 13, 2012

Related U.S. Application Data

(60) Provisional application No. 61/449,819, filed on Mar. 7, 2011.

(51) Int. Cl.
*G01N 27/447* (2006.01)
*B01D 57/02* (2006.01)
*B01D 43/00* (2006.01)

(52) U.S. Cl.
CPC .............. *B01D 43/00* (2013.01); *B01D 57/02* (2013.01); *G01N 27/44769* (2013.01)

(58) Field of Classification Search
CPC ....... G01N 27/447; B01D 57/07; B01D 43/00
USPC ......... 204/456, 468, 605, 610, 618, 467, 454, 204/459, 600, 606, 450; 205/382
See application file for complete search history.

(56) References Cited

U.S. PATENT DOCUMENTS

| | | | |
|---|---|---|---|
| 4,061,560 A * | 12/1977 | Hannig et al. | 204/600 |
| 2004/0050698 A1 * | 3/2004 | Eckerskorn et al. | 204/450 |
| 2004/0256230 A1 | 12/2004 | Yager et al. | |
| 2005/0167269 A1 * | 8/2005 | Updyke et al. | 204/456 |
| 2007/0284250 A1 * | 12/2007 | Magnant et al. | 204/459 |
| 2009/0134031 A1 * | 5/2009 | Ogle | 204/606 |
| 2011/0036718 A1 | 2/2011 | Jung et al. | |

OTHER PUBLICATIONS

H. Wager, "Free-Flow Electrophoresis," Nature, vol. 341, pp. 669-670, Oct. 19, 1989.
Jacob W. Albrecht et al., "Micro Free-Flow IEF Enhanced by Active Cooling and Functionalized Gels," Electrophoresis, vol. 27, pp. 4960-4969 (2006).
Dosil Pereira de Jesus et al., "Microchip Free-Flow Electrophoresis on Glass Substrate Using Laser-Printing Toner as Structural Material," Electrophoresis, vol. 27, pp. 4935-4942 (2006).
Ryan T. Turgeon et al., "Micro Free-Flow Electrophoresis: Theory and Applications," Anal Bioanal Chem, vol. 394, pp. 187-198 (2009).

* cited by examiner

*Primary Examiner* — Jennifer Dieterle
(74) *Attorney, Agent, or Firm* — Eddie E. Scott (57) ABSTRACT

The present invention provides a mechanism for separating or isolating charged particles under the influence of an electric field without metal electrodes being in direct contact with the sample solution. The metal electrodes normally in contact with the sample are replaced with high conductivity fluid electrodes situated parallel and adjacent to the sample. When the fluid electrodes transmit the electric field across the sample, particles within the sample migrate according to their electrophoretic mobility.

10 Claims, 10 Drawing Sheets

LIQUID AND GEL ELECTRODES FOR TRANSVERSE FREE FLOW ELECTROPHORESIS

CROSS-REFERENCE TO RELATED APPLICATIONS

The present application claims benefit under 35 U.S.C. §119(e) of U.S. Provisional Patent Application No. 61/449,819 filed Mar. 7, 2011 entitled "Liquid and Gel Electrodes for transverse Free Flow Electrophoresis (tFFE)," the disclosure of which is hereby incorporated by reference in its entirety for all purposes.

United States Patent Application No. 2011/0036718 filed Aug. 17, 2009 by Byoungsok Jung, Kevin Ness and Klint A. Rose, all of which are inventors in the present application, for Methods for Separating Particles and/or Nucleic Acids using Isotachophoresis, discloses methods related to the present invention. The disclosures of United States Patent Application No. 2011/0036718 filed Aug. 17, 2009 is incorporated herein in its entirety for all purposes by this reference.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates generally to the separation and/or purification of fluids under the influence of an electric field, and specifically, to the separation of charged particles from other fluid constituents according to their mobility within the electric field.

2. State of Technology

Traditionally charged particles have been separated by size or charge using the method of electrophoresis, where an electric field is applied to a sample inserted into agarose gel situated in between two metal electrodes. Once placed under the electric field, the charged particles migrate through the pores of the gel. The end result is bands of particles sorted by their size, with the longer particles traveling less distance through the agarose pores compared to the shorter particles. Analysis of the bands is difficult since the sample is set in the agarose gel, making extraction difficult. In addition, using this technique frequently requires the analyte be heavily preprocessed.

Electrophoresis has also been performed using a capillary tube where when an electric field is applied to the tube, the constituents of the sample migrate at different speeds depending on their electrophoretic mobility in the solution. The result is that over the distance of the tube, the sample concentrates in a particular location based on its electrophoretic mobility relative the other fluid constituents in the tube. When the concentrated sample exits the tube it must be captured. Once captured, the isolated analyte can be further analyzed. One of the problems associated with capillary electrophoresis is that the volume of sample is constrained to about 100 nL, Another problem is that capillary electrophoresis is also labor intensive since capturing the sample from the capillary tube requires attention at the exact moment the concentrated plug of sample exits the capillary.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a mechanism for separating or isolating charged particles under the influence of an electric field without metal electrodes being in direct contact with the sample solution as is seen in current state of the art methods. Removing the metal electrodes from direct contact with the sample eliminates problems created by redox chemistry. These problems include corrosion, oxidation and degradation of electrode materials, gas bubble formation resulting from electrolysis and local solution pH changes that create a pH gradient. The present invention replaces the metal electrodes normally in contact with the sample with high conductivity fluid electrodes situated parallel and adjacent to the flow of the sample. These fluid electrodes can either be liquid or liquid-filled porous electrodes.

In one embodiment the present invention utilizes two high-conductivity liquid electrodes positioned parallel to and sheathing the sample, with one liquid electrode located on each side of the sample. In another embodiment the present invention utilizes liquid-filled porous material as the electrodes. In this embodiment a high-conductivity liquid fills porous material. This high-conductivity liquid is also positioned alongside the porous electrode in order to replenish the high electrolyte ions required to maintain the electrode conductivity.

The present invention has utility in any application where an electric field is used to separate or purify charged particles. Examples of systems into which the present invention could be incorporated include, but are not limited to, a variety of electrophoresis techniques, such as capillary electrophoresis, isotachophoresis, isoelectrofocusing and electric flow-field fractionation. The present invention could be incorporated into these systems or other systems with the objective of manipulating, separating or purifying samples. Such samples could include biological samples, for DNA sequencing, PCR, flow cytometry and pathogen identification. These systems could also be utilized to not only analyze biological samples, but also environmental, clinical or aerosolized samples.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Referring to the drawings, to the following detailed description and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 1:
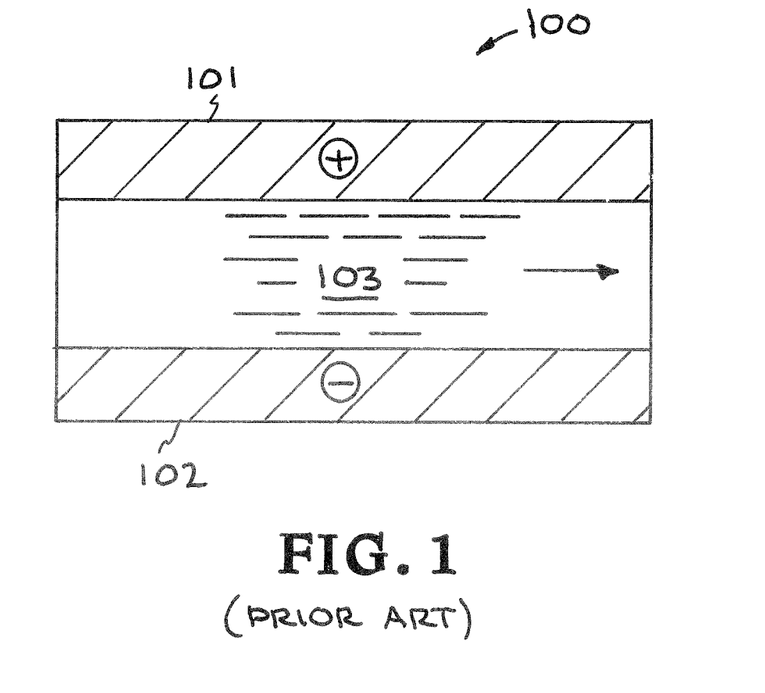
FIG. 1 illustrates the prior art mechanism of zone electrophoresis to separate particles based on their electrophoretic mobility with the use of metal electrodes.

The present invention provides a mechanism for separating or isolating charged particles under the influence of an electric field without metal electrodes being in direct contact with the sample solution as is seen in current state of the art methods. Referring now to the drawings, and in particular to FIG. 1, which illustrates the current state of the art eletrophoretic system designated generally by numeral 100. This system comprises one metal electrode serving as the cathode 101 and another metal electrode serving as the anode 102. These metal electrodes would provide an electric field across the sample 103.

The present invention removes the metal electrodes from direct contact with the sample. This in turn eliminates problems created by redox chemistry occurring at the metal electrodes, which adversely affects the quality of the sample and the ease of sample collection. These problems include corrosion, oxidation and degradation of electrode materials, gas bubble formation resulting from electrolysis and local solution pH changes that create an undesirable pH gradient. The present invention replaces the metal electrodes 101 and 102 normally in direct contact with the sample with high conductivity fluid electrodes. These fluid electrodes can either be liquid or liquid-filled porous electrodes.

The present invention has utility in any application where an electric field is used to separate or purify charged particles. For the purposes of this description of the present invention, the term electrophoresis will be used broadly to encompass all techniques used to separate particles by their elecrophoretic mobility. Examples of systems into which the present invention could be incorporated include, but are not limited to, a variety of electrophoresis techniques, such as capillary electrophoresis, isotachophoresis, isoelectric focusing and electric flow-field fractionation. The present invention could be incorporated into these systems or other systems with the objective of manipulating, separating or purifying samples. Such samples could include biological samples, for DNA sequencing, PCR, flow cytometry and pathogen identification. These systems could also be utilized to not only analyze biological samples, but also environmental, clinical or aerosolized samples.

In one embodiment the present invention utilizes two high-conductivity liquid electrodes. This embodiment is simplified in FIG. 2, with numeral 200 representing the liquid electrode embodiment generally. The liquid electrodes 201 are positioned parallel and adjacent to the electrophoresis chamber walls 202. The liquid electrodes are typically supplied with electrode solution contained in reservoirs 203 remote from the electrophoresis chamber. These reservoirs 203 are connected to the electrophoresis chamber through ion-permeable Nafion tubing 204. The metal electrodes 205 are isolated away from the electrophoresis chamber in the reservoirs 203 where problems associated with redox chemistry are confined to the reservoirs 203. The Nafion tubing 204 is selectively permeable, transmitting the electric potential applied by the metal electrodes 205 to the electrophoresis chamber by preventing the passage of any bubbles generated from the redox chemistry taking place at the metal electrodes 205. While metal electrodes must be isolated from the sample solution within the chamber, they may be positioned in alternate locations to the reservoirs depicted in FIG. 2 provided they are not in direct contact with the sample solution.

Figure 2:
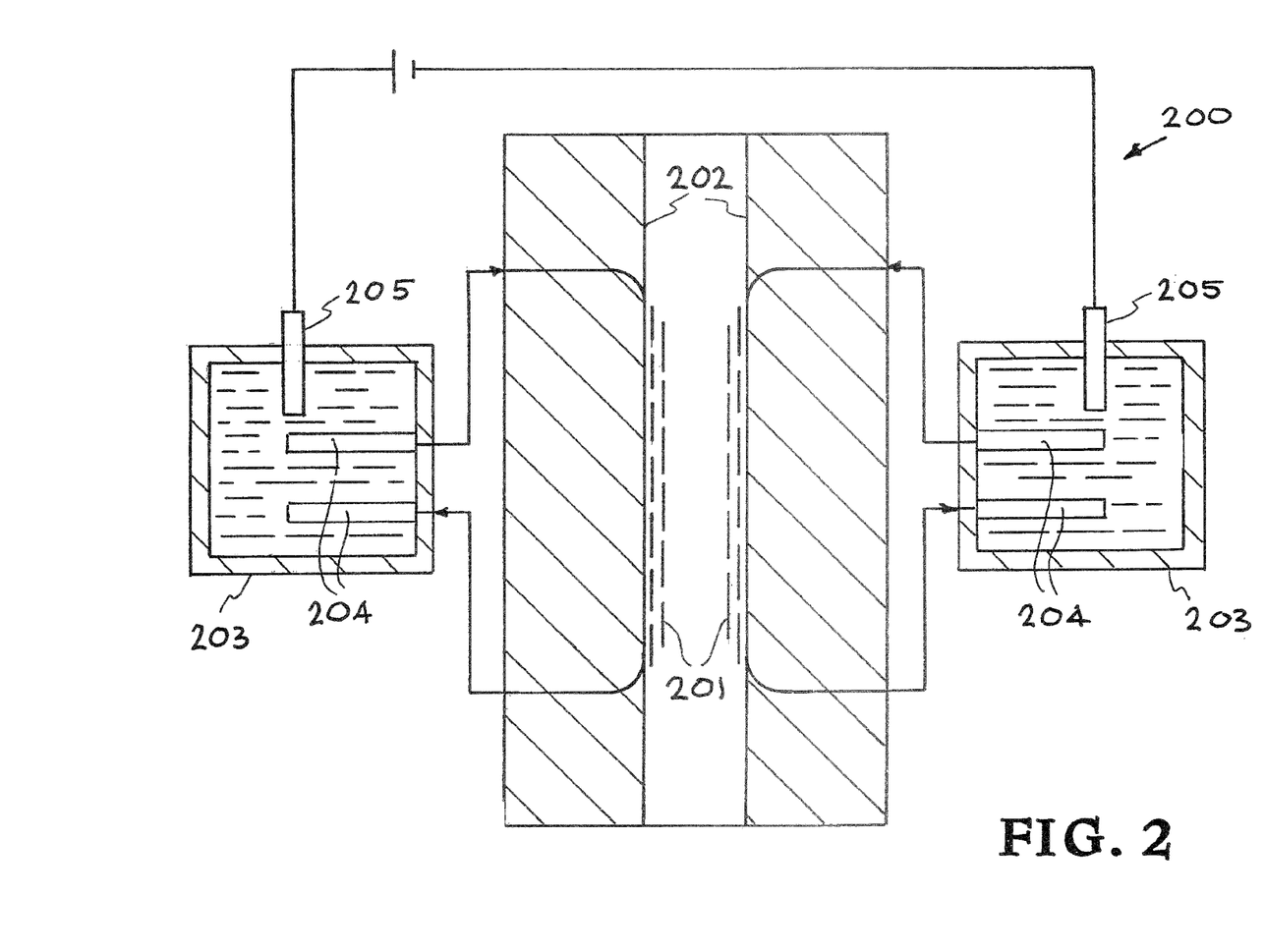
FIG. 2 illustrates a simplified electrophoresis system with liquid electrodes within the electrophoresis chamber.
Figure 3:
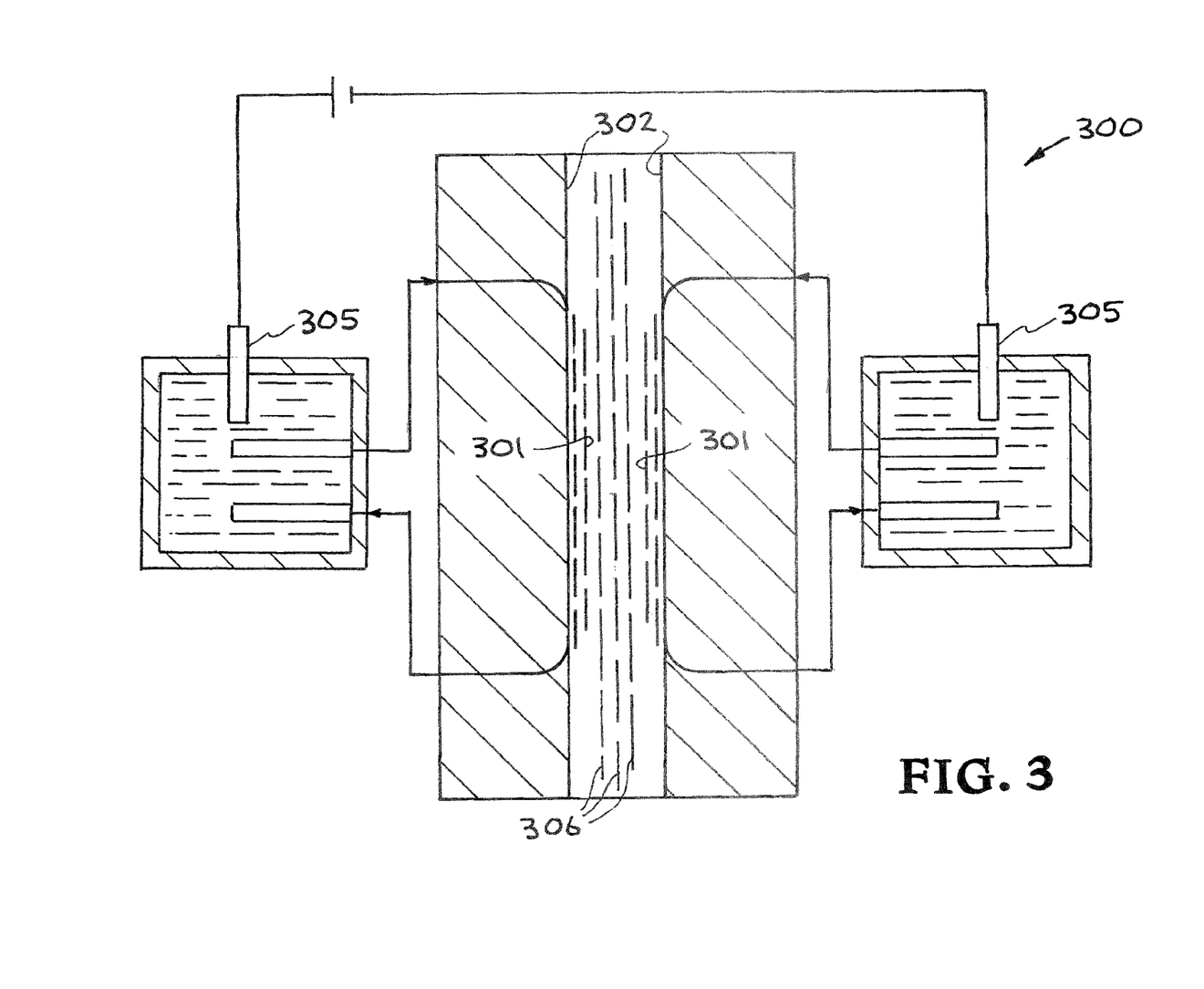
FIG. 3 illustrates a simplified system with liquid electrodes and a sample within the electrophoresis chamber.

FIG. 3 illustrates the liquid electrode embodiment portrayed in FIG. 2 with the addition of the sample. Numeral 300 illustrates this embodiment generally. Here, the high conductivity liquid electrodes 301 sheath the sample 306 with one liquid electrode on each side of the sample and along each side of the chamber wall 302. The liquid electrodes 301 in direct contact with sample 306 serve to transmit the electric field generated at the metal electrodes 305 across the sample. The particles within the sample under the influence of the electric field will then migrate and separate according to their electrophoretic mobilities.

Figure 4:
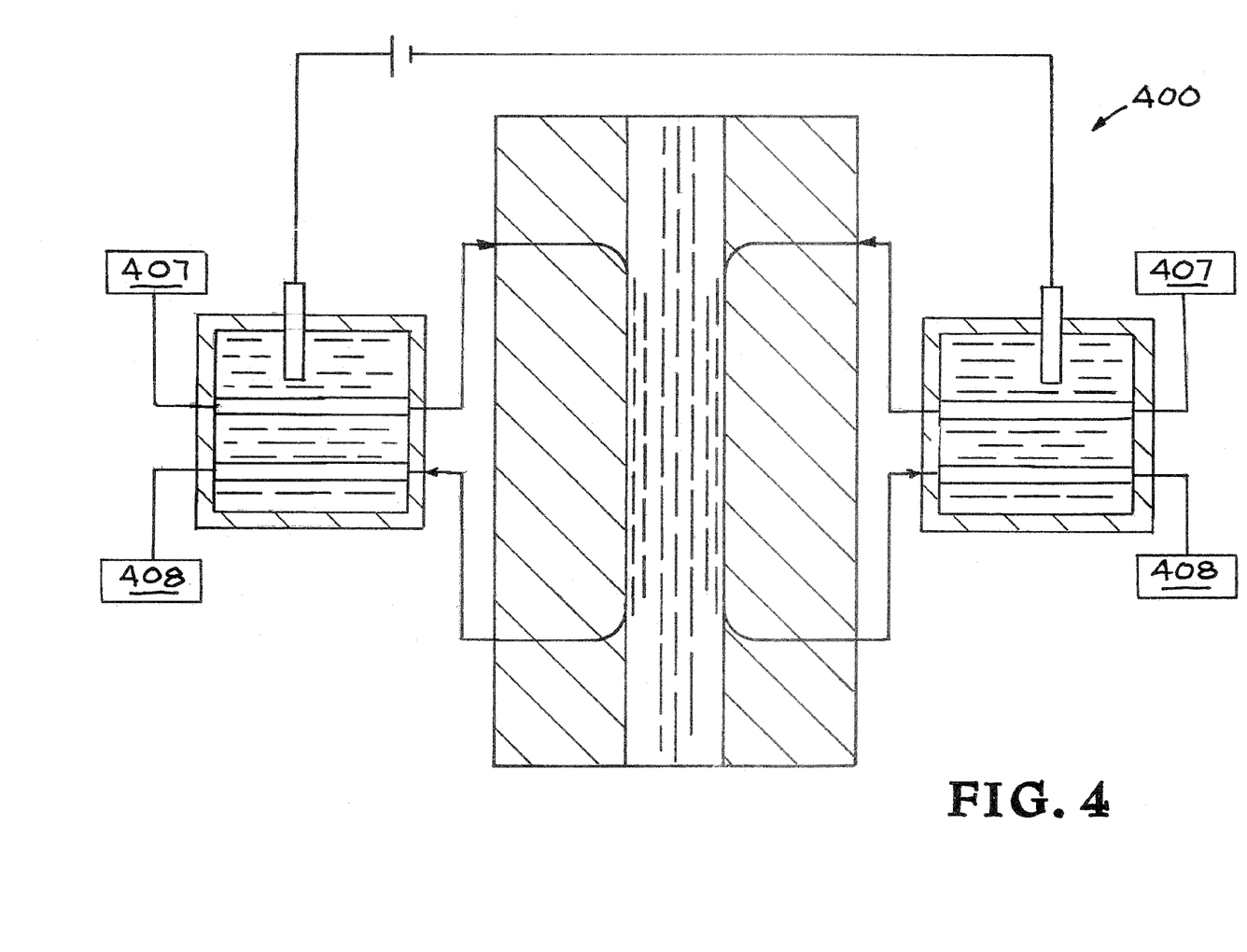
FIG. 4 illustrates the simplified system with flowing liquid electrodes.

An apparatus with liquid electrodes may optionally comprise liquid electrodes flowing through the electrophoresis chamber. A system with flowing liquid electrodes is depicted in FIG. 4, with numeral 400 illustrating the system generally. The liquid electrode flow is typically generated from a device 407 providing pressure to the fluid in the system. Examples of devices that can provide pressure to the system include a pump or syringe. The device generating flow could be positioned downstream from the reservoir. Alternatively, the liquid electrode flow could also be generated using an electroosmotic flow. After the fluid cycles through the system the ion depleted electrode solution is sent to waste 408.

Maintaining liquid electrodes flow enables continuous collection of a sample subsequent to undergoing separation or purification in the electrophoresis chamber. An additional reason to keep the liquid electrodes flowing during sample separation is that fresh electrode solution continuously enters the chamber and consequently the liquid electrodes will maintain a more stable ionic composition and stable conductivity.

The flow of the liquid streams of sample and electrodes within the chamber should be laminar to prevent mixing between the fluid streams. In order to achieve laminar flow, the sample flow rate may need to be adjusted relative to the flow rate of the liquid electrodes. Maintaining a sample flow rate lower than that of the liquid electrodes is sometimes required in order to attain optimal separation of analyte species in the chamber. The applicants have found that performing electrophoresis within a microfluidic, chip-based platform is the preferred platform for this invention. The chamber size and fluid velocity scales associated with microfluidics eliminate turbulent flow. The fluid flow within a microfluid regime typically has a low Reynolds number, which describes a fluid dominated by viscous forces and manifesting a smooth, laminar flow. Further, the non-convective flow pattern keeps the electrodes segregated from the sample for transit times short enough that diffusive mixing remains insignificant.

The liquid electrode should comprise a solution able to conduct the electric field through the sample, such as ionic salt solutions. The higher the conductivity ratio of liquid electrode conductivity to sample solution conductivity, the more metallic-like the liquid electrode will be. Consequently, the liquid electrode conductivity should be as high as possible compared to the sample conductivity. Liquid electrodes with conductivity at least fivefold greater than the sample conductivity have been effective electrodes. Increasing the molarity of the electrode solution to just below the solubility saturation point obtains the highest potential conductivity of a particular liquid electrode solution. Varying the liquid electrode molarity or chemical constituents according to the predicted electrophoretic mobility of the sample solution also helps control the liquid streams.

Any type of high-conductivity solution could be used for the liquid electrodes. Preferred liquid electrode solutions include sodium chloride, 4-(2-hydroxyethyl)-1-piperazineethanesulfonic acid (HEPES), tris(hydroxymethyl) aminomethane (Tris), hydrochloric acid and sodium hydroxide. The selection of liquid electrode solution may depend on the predicted electrophoretic mobility of the sample to be collected. The liquid electrode solution on one side of the chamber may be different than the liquid electrode solution on the opposite side of the chamber. Varying the liquid electrode solution enables control over conductivity as well as the eletrophoretic mobilities of the ions surrounding the sample to be collected. Optionally, a pure buffer solution of known electrophoretic mobility could be introduced to flow adjacent to the sample, which could reduce the possibility of the sample bleeding into the liquid electrode or permit control of the ending sample position in the bulk liquid flow for outlet collection.

In another embodiment the present invention utilizes liquid-filled porous material as the electrodes in direct contact with the sample. In this embodiment the liquid-tilled porous material forms a barrier between the sample solution and the high-conductivity liquid electrolyte solution. This embodiment is simplified in FIG. 5A, with numeral 500 representing the liquid filled porous electrode embodiment generally. The porous material/matrix 509 is positioned adjacent and parallel to the sample 506, sheaths the sample on each side. High conductivity liquid electrolyte solution 501 positioned along each chamber wall 502 should permeate and fill the porous matrix 509, subsequently forming the liquid-filled porous electrode.

Figure 5A:
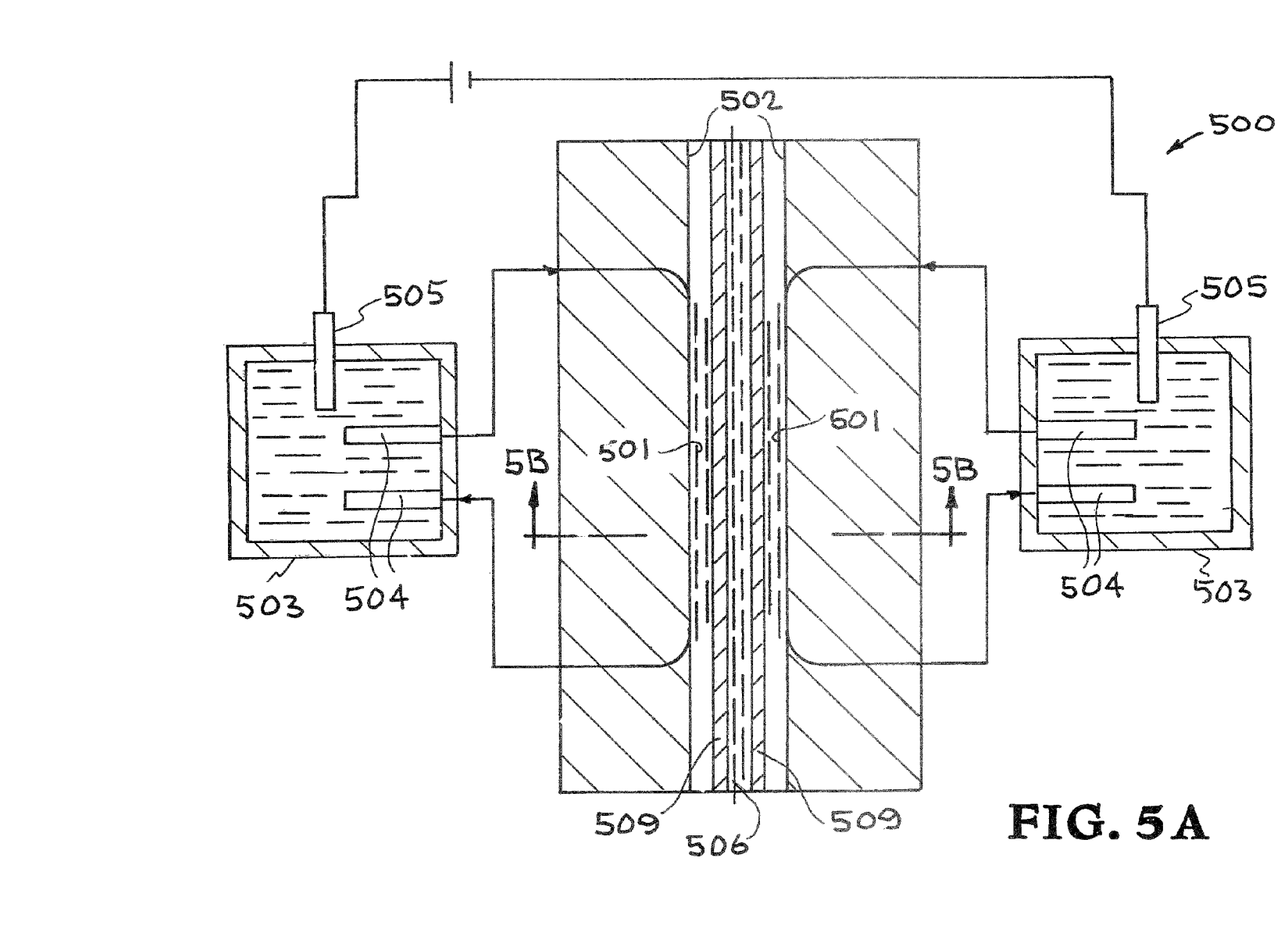
FIG. 5A-5B illustrates a simplified electrophoresis system with liquid filled porous electrodes within the electrophoresis chamber and a cross sectional view of the chamber.

As with the liquid electrode embodiment, high conductivity liquid is supplied to the chamber from reservoirs 503 remote from the electrophoresis chamber. These reservoirs 503 are connected to the electrophoresis chamber through Nafion tubing 504, which delivers the high conductivity liquid along each chamber wall 502. The metal electrodes 505 are isolated away from the electrophoresis chamber in the reservoirs 503 where problems associated with redox chemistry are confined to the reservoirs 503. The Nafion tubing 504 is selectively permeable, transmitting the electric potential applied by the metal electrodes 205 to the electrophoresis chamber only but preventing the passage of any bubbles generated from the redox chemistry taking place at the metal electrodes 505.

Figure 5B:
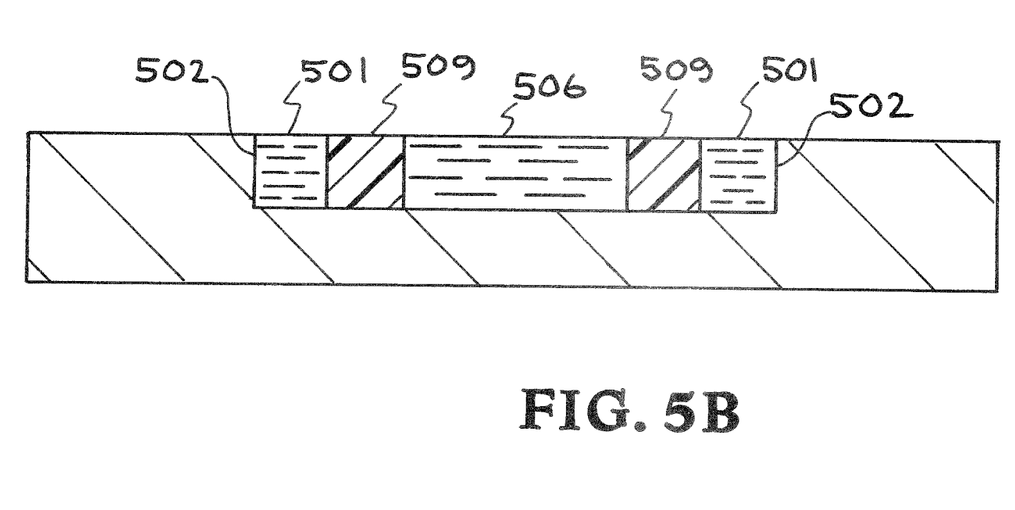

A cross sectional view of the liquid-filled porous electrode is illustrated in FIG. 5B. The high conductivity liquid 501 is positioned adjacent to each of the chamber walls 502. The liquid-filled porous matrix 509 sheaths the sample 506 on each side and forms a barrier between the high-conductivity liquid 501 and the sample solution 506.

An apparatus with liquid-filled porous electrodes may optionally comprise high conductivity liquid flowing through the electrophoresis chamber to replenish the ions and maintain the conductivity of the porous electrode. Maintaining flow within the chamber enables continuous collection of a sample subsequent to undergoing separation or purification in the electrophoresis chamber. An additional reason to keep the liquid electrolyte flowing during sample separation is that fresh electrolyte solution continuously enters the chamber and replenishes the porous matrix with ions for optimal and stable conductivity.

This liquid filled porous material embodiment functions to separate the sample flow from the flow of the high-conductivity liquid streams. This imparts stability to the flow and increases the ease of obtaining laminar fluid flow in the chamber. Ensuring a laminar fluid flow within the chamber reduces mixing between fluid streams. It also increases precision of sample collection downstream. The liquid filled porous material embodiment also functions to facilitate the continuous transfer of ions from high conductivity streams of liquid to the sample streams, which would be impossible with non-porous barriers.

The high conductivity liquid in this liquid-filled porous material embodiment can be any conductive liquid. As in the liquid electrode embodiment, preferred liquid solutions include sodium chloride, 4-(2-hydroxyethyl)-1-piperazineethanesulfonic acid (HEPES), tris(hydroxymethyl)aminoinethane (Tris), hydrochloric acid and sodium hydroxide. The particular selection of high conductivity liquid solution utilized depends on the predicted electrophoretic mobility of the sample to be collected. The liquid electrode solution on one side of the chamber may be different than the liquid electrode solution on the opposite side of the chamber. Varying the chemical composition or molarity of the liquid solution enables control over conductivity as well as the eletrophoretic mobilities of the ions that will be surrounding the sample to be collected.

The porous matrix can be composed of any matrix with pores. A polymer hydrogel, such as polyacrylamide gel has been the preferred porous material. However, other material, such as nitrocellulose, could be substituted. The porous matrix that extends the length of the chamber is preferably as narrow in width as possible while still ensuring the structural stability of the matrix. The minimum width of the porous matrix is confined due to the potential rupture of the material in the event of a pressure imbalance caused by the flow between the chamber and the high-conductivity electrolyte streams.

When acrylamide was the selected porous material, premixed acrylamide solution manufactured by Sigma-Aldrich was preferred. In particular, 30% acrylamide w/v, with a 19:1 monomer:cross-linker ratio has been utilized successfully. Adjustments in this ratio can be made to adjust the rigidity of the gel. The resulting acrylamide solution is then mixed 9:1 with a 2% VA-086 photo-initiator solutions, for a final photo-initiator concentration of 0.2%. In the presence of UV light, the VA-086 splits into free radicals, which catalyze the polymerization and cross-linking of the acrylamide, resulting in the preferred porous material for the current invention, polyacrylamide. While the source of the UV light can vary, applicants utilized a 400 W metal-halide lamp, with an output power at the exposure plane of 60-70 mW/cm$^2$. At this intensity, exposures were completed in 15-20 seconds, compared to exposure times of as long as 15 minutes using other types of sources.

When the polyacrylamide is used on a glass platform, such as the borosilicate glass used for microchip wafers, fixing the gel to the glass may require additional steps. Initially ensuring the glass surface is clean can be accomplished by filling the chamber with 1 M sodium hydroxide for about 10 minutes. Next, the chamber was rinsed with deionized water and then filled with a 5:3:2 mixture of deionized water, glacial acetic acid and 3-(trimethoxysilyl)propyl methacrylate for 30 minutes. Finally, the chamber was rinsed with deionized water followed by 30% acetic acid. The result is that the methacrylate group serves the linker, covalently bonding to the borosilicate glass surface and subsequently bonding with the polyacrylamide gel.

The present invention is further illustrated in the following examples. The examples illustrate some potential variations of the components of the liquid and liquid-filled porous electrodes. The examples provided are a small selection of potential variations of the components of the invention and are not meant to limit the invention to the components shown. For instance, all examples illustrated portray transverse free flow electrophortic techniques on a microchip platform. These examples are provided as illustrations and are not meant to limit the invention from substitution of other techniques and or platforms.

EXAMPLE 1

Figure 6:
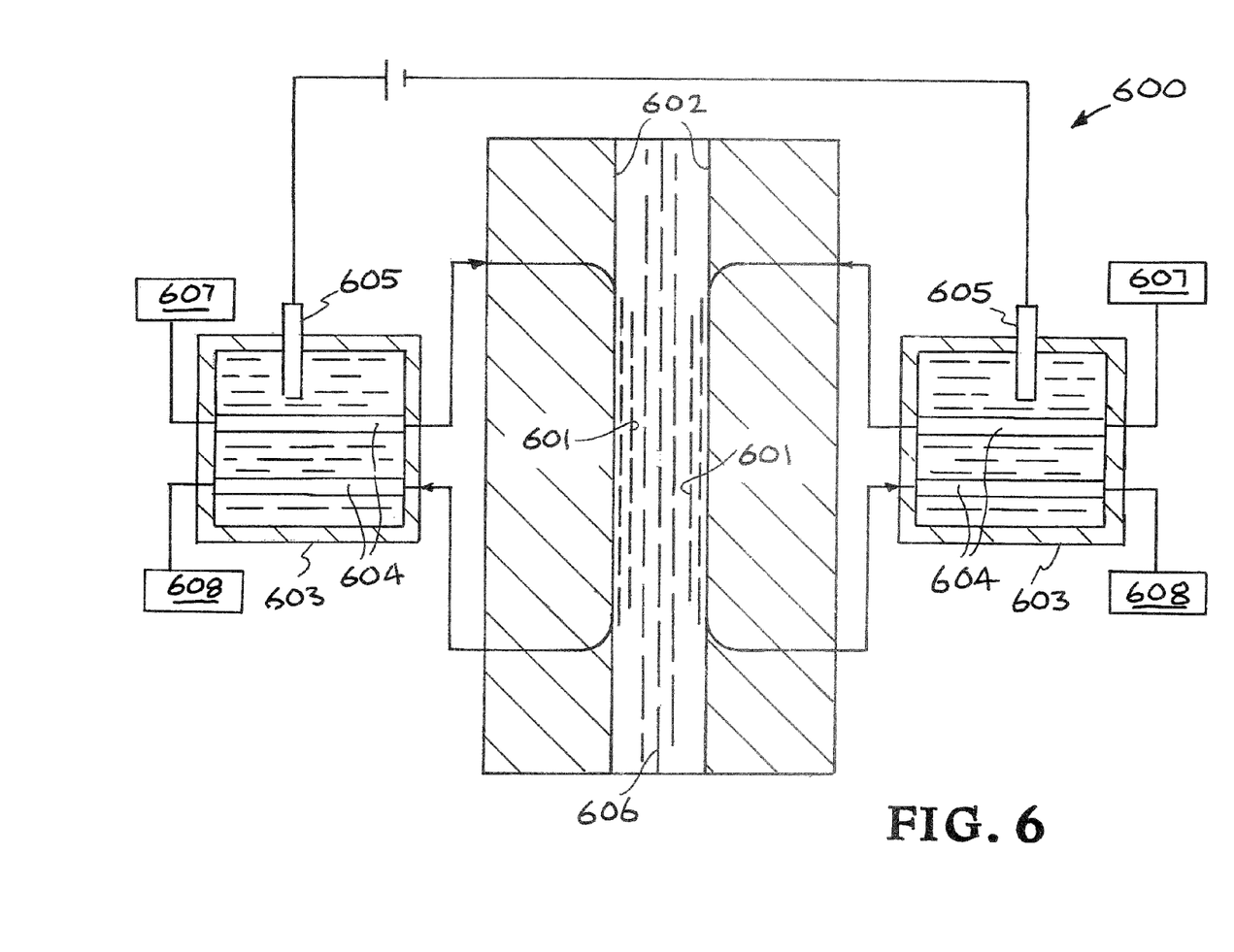
FIG. 6 illustrates an example of the electrophoresis apparatus with liquid electrodes comprising sodium chloride.

In Example 1, the electrophoresis apparatus contains liquid electrodes flowing in a borosilicate glass microchip with the sample subject to simple transverse free-flow electrophoresis. Example 1 is illustrated in FIG. 6, with numeral 600 depicting the apparatus generally. In this example, both liquid electrodes 601 are identically composed of a sodium chloride solution with conductivity equal to 80 mS/cm. The sample 606 conductivity is 10 μS/cm. Fluid flow within the chamber is produced by a pump 607. While the liquid electrodes flow adjacent to the chamber walls 602 at 50 μL/min, the sample 606 flows in between the liquid electrodes at 20 μL/min. The platinum metal electrodes 605 are placed in sodium chloride solution contained in reservoirs 603 located remote from the chamber. Nafion tubing 604 transports the ions from the solution in the reservoirs to the liquid electrode channel on either side of the sample channel. After traveling through the chamber, the liquid electrode solution is carried to waste 608.

EXAMPLE 2

Figure 7:
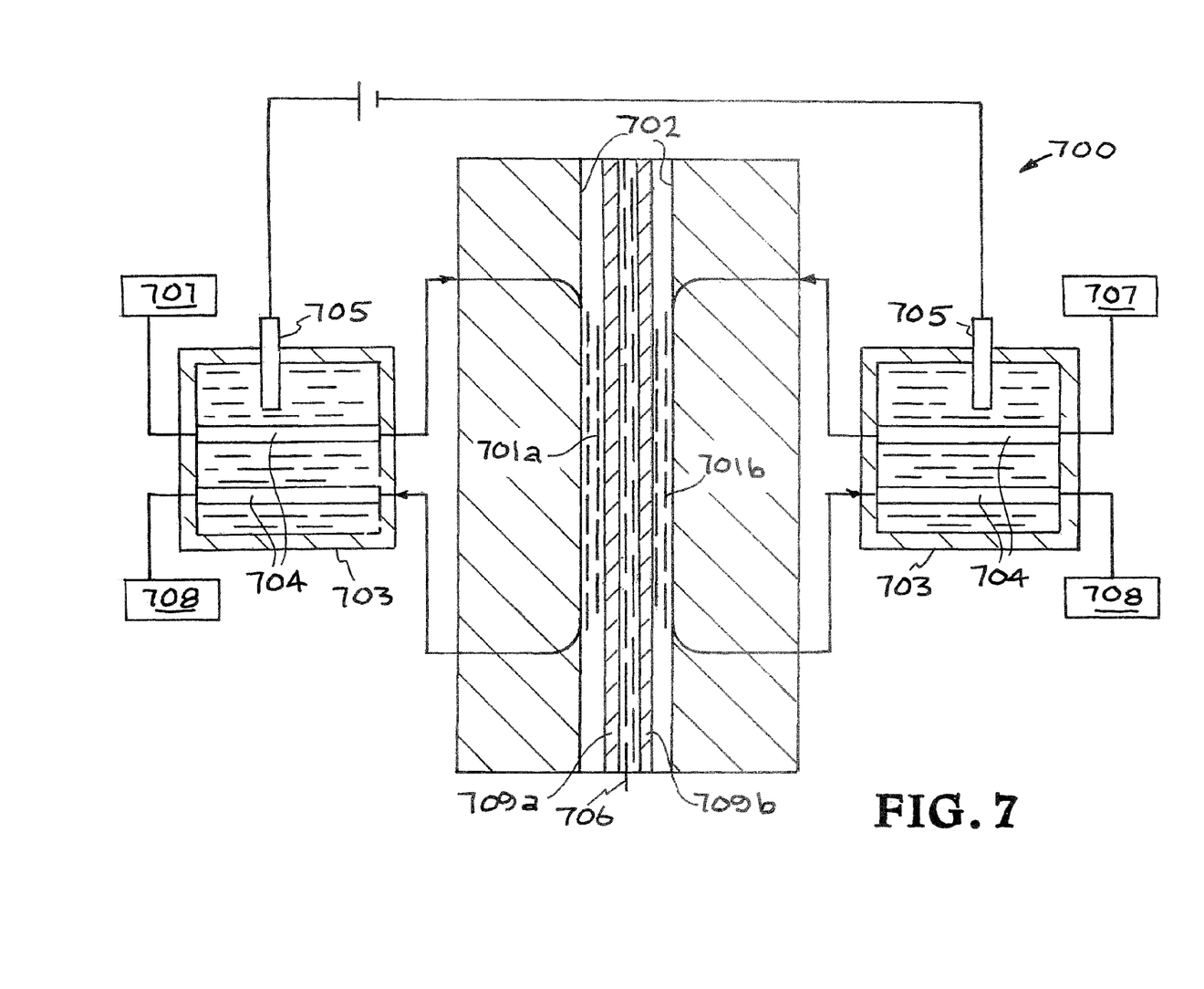
FIG. 7 illustrates an example of the electrophoresis apparatus with liquid-filled porous electrodes comprising porous acrylamide gel filled with liquid electrolyte solution, tris(hyclroxymethyl)aminomethane (Tris)-hydrochloric acid and 4-(2-hydroxyethyl)-1-piperazineethancsullonic acid (HEPES).

In Example 2, the electrophoresis apparatus contains liquid-filled porous electrodes in a borosilicate glass microchip with the sample processed through transverse free flow isotachophoresis. Example 2 is illustrated in FIG. 7, with numeral 700 depicting the apparatus generally. In this example, both liquid-filled porous electrodes are comprised of acrylamide gel. The acrylamide gel 709a in one electrode 701a is filled with tris(hydroxyinethyl)aminomethane (Tris)-hydrochloric acid. This electrode serves as the high-conductivity leading electrolyte. The acrylamide gel 709b in the other electrode 701b is filled with 4-(2-hydroxyethyl)-1-piperazineethanesulfonic acid (HEPES). This electrode serves as the high conductivity trailing electrolyte. Conductivities for the leading and trailing electrolytes range from 20-50 mS/cm. The sample 706 conductivity is 0.3 ms/cm. Fluid flow within the chamber is produced by a pump 707.

While the liquid electrolyte 701a and 701b entering the chamber adjacent to each of the chamber walls 702 flows at 50-100 μL/min, the sample 706 flows in between the liquid electrodes at 25-100 μL/min. The platinum metal electrodes 705 are placed in corresponding liquid electrolyte solution contained in reservoirs 703 located remote from the chamber. Nafion tubing 704 transports the ions from the solution in the reservoirs to the liquid electrode channel on either side of the sample channel. After traveling through the chamber, the liquid electrode solution is carried to waste 708.

EXAMPLE 3

Figure 8:
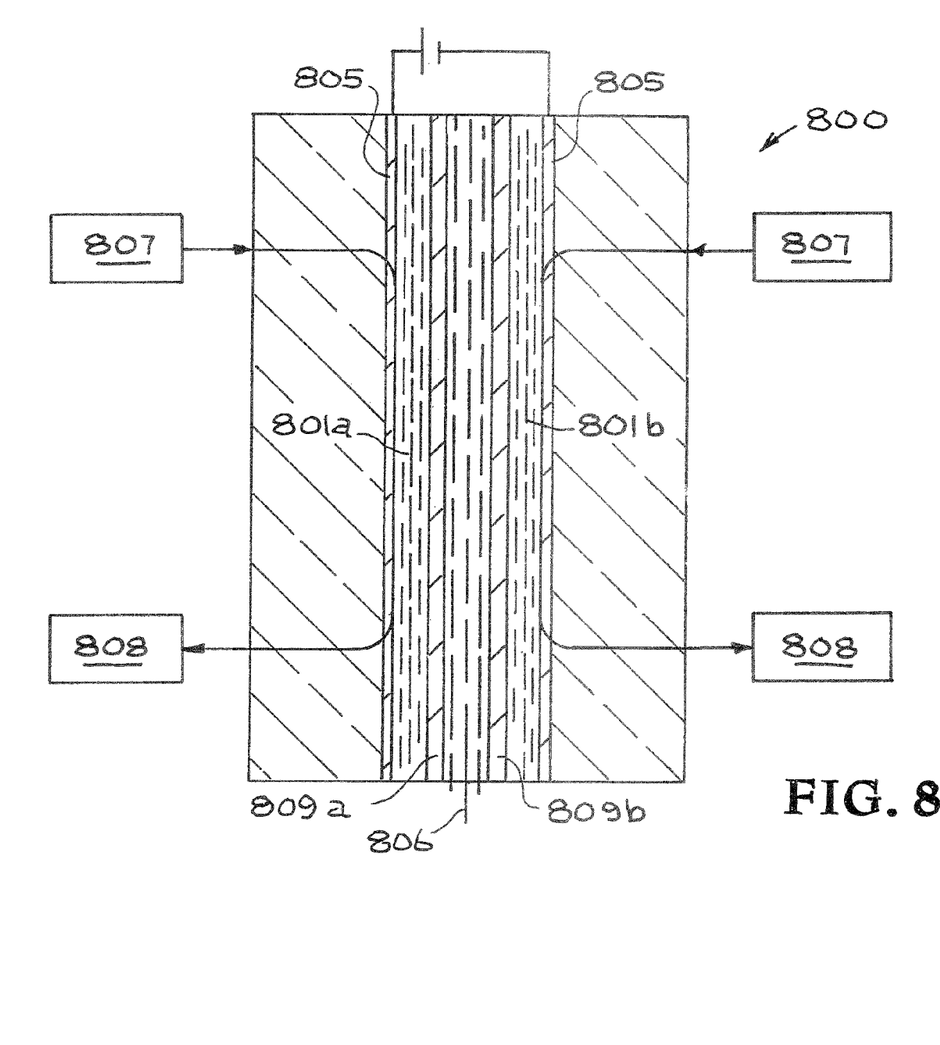
FIG. 8 illustrates a variation of the electrophoresis apparatus of FIG. 7 with the metal wires routed onto the microchip awash in the liquid electrolyte solution.

In Example 3, the electrophoresis apparatus contains liquid-filled porous electrodes in a borosilicate glass microchip with the sample processed through transverse free flow isotachophoresis. This example differs from Example 2 in that the metal electrodes are placed on the microchip. Example 3 is illustrated in FIG. 8, with numeral 800 depicting the apparatus generally. In this example, both liquid-filled porous electrodes are comprised of acrylamide gel. The acrylamide gel 809a in one electrode is filled with liquid electrolyte 801a comprising tris(hydroxymethyl)aminomethane (Tris)-hydrochloric acid. This electrode serves as the high-conductivity leading electrolyte. The acrylamide gel 809b in the other electrode is filled liquid electrolyte 801b comprising 4-(2-hydroxyethyl)-1-piperazineethancsulfonic acid (HEPES). This electrode serves as the high conductivity trailing electrolyte. Conductivities for the leading and trailing electrolytes range from 20-50 mS/cm. The sample 806 conductivity is 0.3 ms/cm. Fluid flow within the chamber is produced by a pump 807.

While the liquid electrolyte 801a and 801b entering the chamber adjacent to each of the chamber walls flows at 50-100 μL/min, the sample 806 flows in between the liquid electrodes at 25-100 μL/min. The platinum metal wires 805 are placed on the chip running the length of the chamber adjacent to the liquid electrolyte solution. Ions can be supplied using standard tubing from the solution in the reservoirs to the liquid electrode channel on either side of the sample channel to continually bathe the metal wires 805 with fresh electrolyte solution. After traveling through the chamber, the liquid electrode solution is carried to waste 808.

EXAMPLE 4

Figure 9:
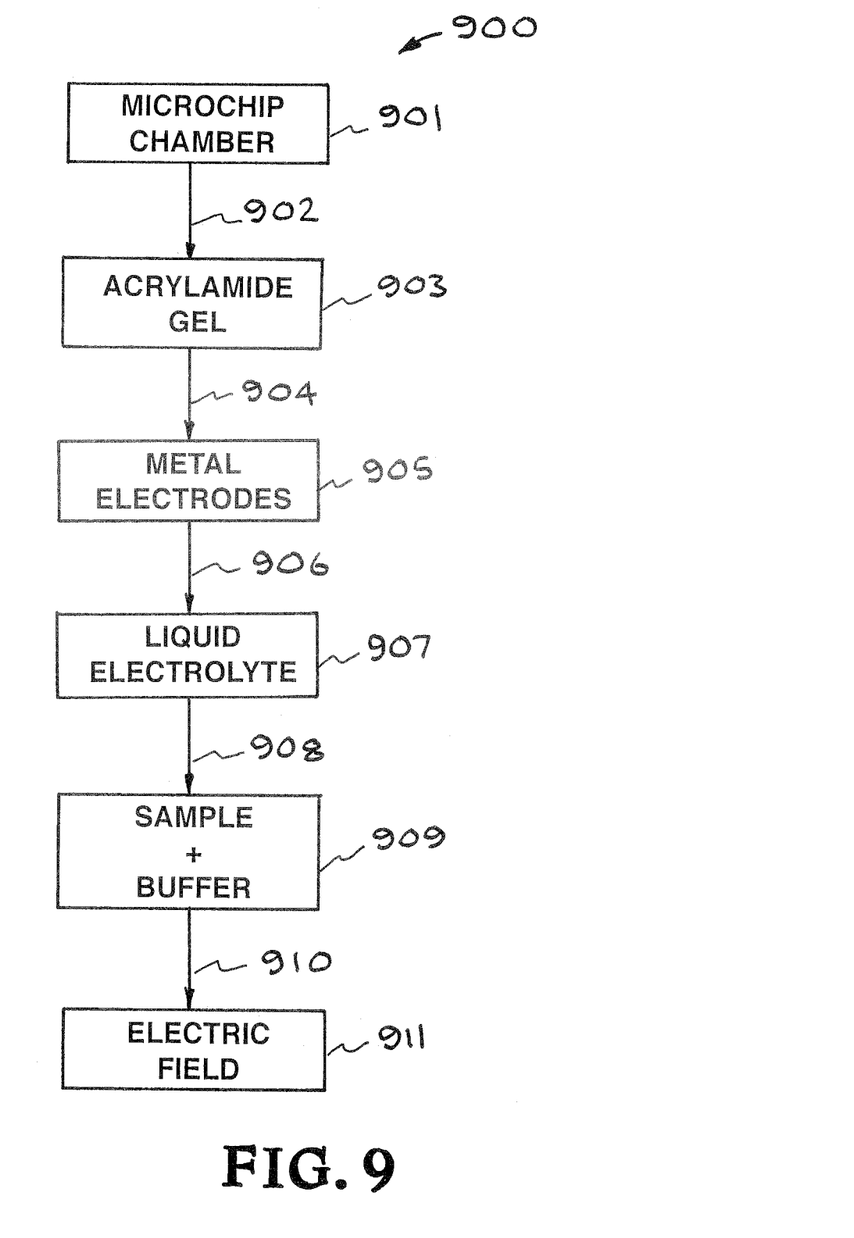
FIG. 9 illustrates a flowchart for the method of transverse free flow isotachophoresis using acrylamide gel for the liquid-filled porous electrodes.

The method for transverse free flow isotachophoresis using polyacrylamide gel for the liquid-filled porous electrodes is illustrated in flowchart depicted in FIG. 9 and is designated generally by the number 900. The steps of the method are as follows:

Step 1. (Reference Numeral 902)—The clean glass on the microchip chamber 901 is prepared with 3-(trimethoxysilyl)

propyl methacrylate which bonds to the glass surface of the microchip chamber 901 and then to any polyacrylamide gel 903 later applied.

Step 2. (Reference Numeral 904)—Polyacrylamide Gel 903 is prepared in order to affix the gel onto the microchip chamber 901. The method 900 is designed to keep problems associated with metal redox chemistry typically occurring at the metal electrodes isolated from the sample through polyacrylamide gel 903 barriers sheathing the sample 909.

Step 3. (Reference Numeral 906)—Metal electrodes 905 are placed in liquid electrolyte 907 reservoirs located remote from the microchip chamber. Nafion tubes transport the liquid electrolyte 907 into the microchip chamber 901.

Step 4. (Reference Numeral 908)—Two separate liquid electrolyte 907 streams are transported into the microchip chamber 901 along each chamber wall, parallel and distal to the polyacrylamide gel 903. Liquid electrolyte 907 permeates the pores of the polyacrylamide gel 903, which conducts the electric field 911 to the sample 909. The secure fixture of polyacrylamide gel 903 achieved in step 904 to ensure the gel will not collapse under the pressure of the flow from the sample 909.

Step 5. (Reference Numeral 910)—Sample solution, with an optional adjacent pure buffer solution, is flowed parallel and in between microchamber 901 wall and the polyacrylamide gel 903 barriers. Once the electric field 910 is activated, particles in the sample migrate according to their electrophoretic mobility and are ready for collection.

As previously discussed, the present invention provides a mechanism for separating or isolating charged particles under the influence of an electric field without metal electrodes being in direct contact with the sample solution. In one of its broadest aspects the present invention provides a device for separating a charged analyte, comprising: a chamber; a first fluid electrode within said chamber positioned along a chamber wall; a second fluid electrode within said chamber positioned along a second chamber wall opposite first chamber wall; and an electric field generated from external circuitry applied to said first fluid electrode and said second fluid electrode perpendicular to said first chamber wall and said second chamber wall. The liquid of the first fluid electrode and the second fluid electrode flows in the device for separating a charged analyte. In one embodiment pressure creates said flow. In another embodiment said flow is electroosmotic. In yet another embodiment the flow is produced by a displacement pump, which can be a syringe. In one embodiment said liquid is an ionic solution. In another embodiment said ionic solution is sodium chloride. In yet another embodiment said ionic solution is HEPES. In another embodiment said ionic solution is hydrochloric acid. In another embodiment said ionic solution is sodium hydroxide. In another embodiment said ionic solution is Tris. In one embodiment said first fluid electrode and said second fluid electrode are a porous, liquid filled matrix. In another embodiment said porous, liquid filled matrix is a gel polymer matrix. In yet another embodiment said gel polymer matrix is polyacrylamide.

The present invention also provides a method for separating a charged analyte, comprising the steps of: flowing a first fluid electrode into a separation chamber adjacent the separation chamber wall and parallel to said analyte flow; flowing a second fluid electrode into a separation chamber adjacent to the other separation chamber wall and parallel to said analyte flow; simultaneously flowing a purified ionic salt solution positioned adjacent and parallel to flow of said analyte and in between said first fluid electrode and second fluid electrode; applying an electric field generated from external circuitry to said first fluid electrode and said second fluid electrode wherein said electric field is applied perpendicular to the flow of said analyte; and applying electric field creates migration and concentration of said charged analyte in a direction perpendicular to the bulk flow in said separation chamber. In the method said fluid electrode is a liquid. In one embodiment of the method said liquid is an ionic salt solution. In another embodiment of the method said ionic salt solution is sodium chloride. In one embodiment of the method said fluid electrode is a porous, liquid filled matrix. In another embodiment of the method said porous, liquid filled matrix is a gel polymer matrix. In yet another embodiment of the method said gel polymer matrix is polyacrylamide.

In one embodiment the present invention provides a device for separating a charged analyte, comprising: a separation chamber; a first fluid electrode within said separation chamber positioned along a separation chamber wall, parallel to flow of said analyte; a second fluid electrode within said separation chamber positioned along the other separation chamber wall, parallel to flow of said analyte; wherein conductivity of each said fluid electrode conductivity exceeds conductivity of said analyte; a purified ionic salt solution positioned between said first and said second fluid electrode, adjacent and parallel to flow of said analyte; and an electric field generated from external circuitry applied to said first fluid electrode and said second fluid electrode perpendicular to the bulk fluid flow in said separation chamber. In one embodiment of the device said fluid electrode is a liquid. In another embodiment of the device said liquid is an ionic salt solution. In yet another embodiment of the device said ionic salt solution is sodium chloride. In one embodiment of the device said fluid electrode is a porous, liquid filled matrix. In another embodiment of the device said porous, liquid filled matrix is a gel polymer matrix. In yet another embodiment of the device said gel polymer matrix is polyacrylamide.

Electrophoresis is carried out by applying an electric field across a certain region of solution containing the sample to be analyzed/manipulated, causing migration of charged particles. This invention can be implemented with transverse free-flow electrophoresis (FFE) in which the electric field is applied at right angles to the flow direction of analyte flowing through a channel (without a sieving matrix), for the purposes of sorting or extracting different types of particles (e.g. viruses vs. cells, vs. peptides and nucleic acids). This is readily accomplished since free-solution electrophoretic mobility depends mainly on particle size and charge.

As previously discussed, one embodiment of this invention ("liquid electrode" or LE), takes advantage of laminar fluid flow characteristics within microfluidic channels. Two streams of highly-conductive solution (with conductivity $\sigma_{LE}$ at least fivefold greater than the sample $\sigma_s$) are directed into the same channel, sheathing the sample of interest on both sides. The non-convective flow pattern keen the electrodes segregated from the sample (for transit times short enough that diffusive mixing remains insignificant). We have demonstrated functional liquid electrodes capable of manipulating fluorescent dye molecules. This approach requires precise flow control of both sample buffer and LE fluid, as well as careful electrode design to maintain a uniform electric field.

Another potential embodiment of this invention involves filling the area on either side of the main flow channel with an electrolyte-containing polymer hydrogel ("gel electrode" or GE). To replenish the high concentration of electrolyte ions required to maintain GE conductivity, a stream of high-conductivity buffer is passed along the side of each GE distal to the main flow channel (for short-lifetime applications such as disposable devices, the flow-through buffer can be omitted).

The GE scheme relaxes the flow-control requirements of the LE, but requires additional fabrication steps.

Electrical contact from external circuitry is made to the LE or GE by means of conventional metal electrodes (such as Pt or Au), at sites away from the main flow channel (or off-chip). The high conductivity of the LE/GE electrolyte ensures minimal resistive drop in the electrode, allowing nearly the full applied voltage to be applied across the main flow channel.

This invention can be used with transverse-mode free-flow isotachophoresis, among other methods of electrophoresis.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An electrophoresis apparatus for separating particles in a flowing liquid sample, comprising:
    a microchip;
    a chamber in said microchip, said chamber having a first chamber wall and a second chamber wall wherein said flowing liquid sample is between said first chamber wall and said second chamber wall;
    a first reservoir containing a first conductive liquid;
    a first metal electrode in said first reservoir in contact with said first conductive Liquid;
    a first pump connected to said first reservoir for pumping said first conductive Liquid;
    a first flowing conductive liquid electrode within said chamber connected to said first conductive liquid and said first pump wherein said first flowing conductive liquid electrode is positioned along said first chamber wall and positioned wherein the flowing liquid sample is in direct contact with said first flowing conductive liquid electrode;
    a second reservoir containing a second conductive liquid;
    a second metal electrode in said second reservoir in contact with said second conductive liquid;
    a second pump connected to said second reservoir for pumping said second conductive liquid;
    a second flowing conductive liquid electrode within said chamber connected to said second conductive liquid and said second pump wherein aid second flowing conductive liquid electrode is positioned along said second chamber wall opposite first chamber wall and positioned wherein the flowing liquid sample is in direct contact with said second flowing conductive liquid electrode; and
    an electric field generated from associated circuitry applied to said first flowing conductive liquid electrode and said second flowing conductive liquid electrode.

2. The electrophoresis apparatus of claim 1 wherein said microchip is a borosilicate glass microchip.

3. The electrophoresis apparatus of claim 1 wherein said first conductive liquid and said second conductive liquid are liquid sodium chloride solutions.

4. The electrophoresis apparatus of claim 1 wherein said first conductive liquid and said second conductive liquid are sodium chloride solutions with conductivity equal to 80 mS/cm.

5. The electrophoresis apparatus of claim 1 wherein said first metal electrode and said second metal electrode are platinum metal electrodes.

6. The electrophoresis apparatus of claim 1 wherein said first flowing liquid electrode and said second flowing liquid electrode are flowing conductive sodium chloride solutions electrodes.

7. The electrophoresis apparatus of claim 1 wherein said first pump and said second pump are position to provide a source of pressure that produces said first flowing liquid electrode and said second flowing liquid electrode.

8. The electrophoresis apparatus of claim 1 wherein said first pump and said second pump are position to provide a source of pressure that pumps said first conductive liquid and said second conductive liquid and produces said first flowing conductive liquid electrode and said second flowing conductive liquid electrode.

9. The electrophoresis apparatus of claim 1 wherein said first flowing conductive liquid electrode is positioned immediately adjacent to said first chamber wall and said second flowing conductive liquid electrode is positioned immediately adjacent to second chamber wall and wherein the flowing liquid sample is sheathed between said first flowing conductive liquid electrode and said second flowing conductive liquid electrode and wherein the flowing liquid sample is in direct contact with said first flowing conductive liquid electrode and said second flown conductive liquid electrode.

10. An electrophoresis apparatus for separating particles in a flowing liquid sample, comprising:
    a microchip;
    a chamber in said microchip, said chamber having a first chamber wall and a second chamber wall wherein said flowing liquid sample is between said first chamber wall and said second chamber wall;
    a first reservoir containing a first liquid sodium chloride solution:
    a first metal electrode in said first reservoir in contact with said first liquid sodium chloride solution;
    a first pump connected to said first reservoir for pumping said first liquid sodium chloride solution;
    a first flowing liquid sodium chloride solution electrode within said chamber connected to said first sodium chloride solution and said first pump wherein said first flowing liquid sodium chloride solution electrode is positioned along said first chamber wall for producing a cathode electrode and is positioned wherein the flowing liquid sample is in direct contact with said first flowing liquid sodium chloride solution electrode;
    a second reservoir containing a second liquid sodium chloride solution;
    a second metal electrode in said second reservoir in contact with said second liquid sodium chloride solution;
    a second pump connected to said second reservoir for pumping said second liquid sodium chloride solution;
    a second flowing liquid sodium chloride solution electrode within said chamber connected to said second sodium chloride solution and said second pump wherein said second flowing liquid sodium chloride solution electrode is positioned along said second chamber wall opposite said first chamber wall for producing an anode electrode and is positioned wherein the flowing liquid sample is in direct contact with said second flowing liquid sodium chloride solution electrode; and
    an electric field applied to said first flowing liquid sodium chloride solution electrode means and said second flowing liquid sodium chloride solution electrode.

* * * * *